(12) United States Patent
Ferreira et al.

(10) Patent No.: US 8,709,004 B2
(45) Date of Patent: Apr. 29, 2014

(54) METHOD AND DEVICE FOR VASCULAR TREATMENT

(75) Inventors: Julio H. G. Ferreira, Porto Alegre (BR);
Jorge O. Löpez D'Ambola, Mendoza (AR); Wolfgang Neuberger, Dubai (AE); Antonio C. Reichelt, Porto Alegre (BR); Jorge E. Soracco, Capital Federal (AR)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 577 days.

(21) Appl. No.: 12/755,948

(22) Filed: Apr. 7, 2010

(65) Prior Publication Data
US 2011/0196354 A1    Aug. 11, 2011

(51) Int. Cl.
*A61B 18/18*    (2006.01)
(52) U.S. Cl.
USPC .................................. 606/14; 372/15; 372/22

(58) Field of Classification Search
USPC ............................... 372/2, 10, 13–16, 21, 22
See application file for complete search history.

(56) References Cited

U.S. PATENT DOCUMENTS

2003/0109869 A1*    6/2003    Shadduck .................. 606/41
2009/0248011 A1*    10/2009   Hlavka et al. ............ 606/41

\* cited by examiner

*Primary Examiner* — Armando Rodriguez
(74) *Attorney, Agent, or Firm* — Bolesh J. Skutnik; BJ Associates (57) ABSTRACT

A method and device for improved minimally invasive vascular treatments. The method comprises introducing a catheter into a vein to be treated. The catheter is adapted to introduce an energy transmitting member and a fluid into the vein to be treated. The fluid introduced via the catheter can include, but is not limited to: saline solutions, cooled saline solutions, liquids for vapor generation, vasoconstricting agents, anesthetic agents and/or a formulation containing an ingredient which can be activated by the applied energy.

27 Claims, 8 Drawing Sheets

METHOD AND DEVICE FOR VASCULAR TREATMENT

DOMESTIC PRIORITY UNDER 35 USC 119(e)

This application claims the benefit and priority of U.S. Provisional Application Ser. No. 61/168,094 filed Apr. 9, 2009, entitled "Method and Device for Vascular Treatment" by Wolfgang Neuberger, Jorge Soracco, Jorge Lopez D'Ambola, Julio H. G. Ferreira, and Antonio Carlos Reichelt, which is incorporated by reference herein.

BACKGROUND OF THE INVENTION

1. Field of the Invention

The present invention relates to laser endovascular treatments and in particular, to the treatment of vascular pathologies, such as venous insufficiency, with laser energy using an optical fiber set and low power densities.

2. Invention Disclosure Statement

The human venous system of the lower limbs consists essentially of the superficial venous system and the deep venous system, both connected by perforating veins. The superficial system comprises the great and the small saphenous veins, while the deep venous system includes the anterior and posterior tibial veins, which converge to form the popliteal vein near the knee. The popliteal vein, in turn, becomes the femoral vein when joined by the small saphenous vein.

The venous system comprises valves, whose main function is to achieve unidirectional blood flow back to the heart. Venous valves are usually bicuspid valves, with each cusp forming a blood reservoir, which force their free surfaces together under retrograde blood pressure. As a consequence, when properly operating, retrograde blood flow is prevented, allowing only antegrade flow to the heart. A valve becomes incompetent when their cusps are unable to seal properly under retrograde pressure gradient, so retrograde blood flow occurs. When retrograde blood flow occurs, pressure increases in the lower venous sections, dilating veins and usually leading to additional valvular failure.

Valvular failure, usually referred to as venous insufficiency, is a chronic disease that can lead to skin discoloration, varicose veins, pain, swelling and ulcerations. Varicose veins refer to blood vessels that have become enlarged and twisted and have progressively lost their wall elasticity. Owing to the widening of the blood vessels, vein valves cannot be completely closed and veins lose their ability to carry blood back to the heart. This leads to an accumulation of blood inside the vessels, enlarging and twisting the veins even more. Furthermore, varicose veins usually have a blue or purple color and may protrude twisted above the surface of the skin, being responsible of their characteristically unattractive appearance. They are commonly formed in the superficial veins of the legs, which are subject to high pressure when standing. Other types of varicose veins include venous lakes, reticular veins and telangiectasias.

There is a number of treatments available intending to eradicate these kinds of vascular pathologies. Some of them only consist in relief of symptoms because they do not prevent new varicose veins from forming. These include elevating the legs by lying down or using a footstool when sitting, elastic stockings and exercise.

Varicose veins are frequently treated by eliminating the insufficient veins. This forces the blood to flow through the remaining healthy veins. Various methods can be used to eliminate the problem insufficient veins, including sclerotherapy, surgery, electro-cautery, and laser treatments.

Sclerotherapy uses a fine needle to inject a solution directly into the vein. This solution irritates the lining of the vein, causing it to swell and the blood to clot. The vein turns into scar tissue that fades from view. Some physicians treat both varicose and spider veins with sclerotherapy. The sclerosant acts upon the inner lining of the vein walls causing them to occlude and block blood flow. This method has numerous complications. People with allergies may suffer allergic reactions, occasionally severe. The sclerosant may burn the skin, if the needle is not properly inserted or permanently mark or stain the skin. Furthermore, sclerotherapy can lead occasionally to blood clots. Moreover, treatment is limited to veins of a particular size and range as larger varicose veins may be more likely, according to many studies, to recur if treated with sclerotherapy.

Surgery to treat varicose veins, commonly referred to as "stripping," is usually done under local or partial anesthesia. Here, the problematic veins are stripped out by passing a flexible device through the vein and removing it through an incision near the groin. Smaller tributaries of these veins also are stripped with this device or removed through a series of small incisions. Those veins that connect to the deeper veins are then tied off. Surgery also results in scarring where small incisions are made and may occasionally cause blood clots. Furthermore, procedures are long and require long recovery periods.

These surgical therapies show several disadvantages compared to other approaches. One of them is the need of general, loco-regional or peridural anesthesia. Furthermore, these procedures may damage collateral branches of the vein which may consequently bleed, giving rise to hematomas, or may lead to other complications such as blood loss, pain, infection, nerve injury and swelling. Moreover, because of the damage done to the treated area, patients may have pain and discomfort for hours and even days after surgery. Side effects of this method of removing varicose veins are those for any surgery performed under anesthesia, including nausea, vomiting, and the risk of wound infection.

Another well known method of treating insufficient veins is through the use of radio frequency (RF). An example of the application of this method can be found in U.S. Patent Publication No. 2006/0069471, by Farley et al. Electrodes are introduced through a catheter inside the vein to be treated for insufficiency and RF is applied to cause selective heating of the vein. The catheter is positioned within the vein to be treated and the electrodes on the catheter are moved toward one side of the vein. RF energy is applied in a directional manner from electrodes at the working end of a catheter to cause localized heating and corresponding shrinkage of the adjacent venous tissue. This method has some disadvantages. The use of RF energy in the treatment of vein insufficiency may be ineffective in certain cases and interventions can be lengthy and stressful for the patient. Nevertheless, it is still a popular local energy treatment among physicians. There are minimally invasive surgical options for the treatment of blood vessels. The alternatives preferred by those skilled in the art are those that use laser radiation. Laser surgery has been improved due to new diode laser systems. For endovascular laser surgery, laser radiation applies thermal energy to the vein with the aid of an optical fiber, and while it is withdrawn the vein closes and eventually disappears through absorption. In these and other cases, endovascular laser treatment provides an effective technique for eliminating skin and vascular problems. Moreover, it still provides a closer access to the treatment area, allowing less powerful laser equipments and less skin or healthy tissue damage. This in turn reduces costs while at the same time provides a shorter recovery period due to less damage of skin and surrounding healthy tissue.

In most cases, endovascular laser treatment can be summarized as follows: first of all, a guide wire is inserted into the vein to be treated, preferably with the help of an entry needle. Secondly, an introducer sheath and catheter are inserted together over the guide wire. Then the introducer sheath combination is advanced to a desired position. When it is properly positioned, the guide wire first and then the introducer sheath are removed leaving the catheter in place. Subsequently, the optical laser fiber (coupled to a laser source) is inserted into the catheter and positioned so the fiber's distal tip and the catheter are at the same point. After that, anesthesia is applied. Usually tumescent anesthesia is applied to the vein to be treated for isolating the vein from perivenous tissue and diminishing vein diameter. Previous to lasing, the catheter is pulled back so that the distal end of the fiber is exposed near the treatment area of the vein. Finally, the laser source is activated to irradiate vein interior while slowly withdrawing laser fiber and catheter together, at a rate, e.g., of 2 to 3 mm per second, to treat and close a desired length of the vein.

In U.S. Patent Publication No. 2007/0260229, Navarro et al. disclose a method and kit for endovenous laser treatment in which previous to applying energy, a sclerosing agent is injected into the vein. Sclerosing agent irritates the inner layers of the vein causing it to collapse. This makes posterior lasing more effective. Sclerosing agents do not however, have an analgesia effect and therefore anesthesia must be applied in addition to this, making the procedure more complex and longer lasting. Furthermore, this method has the disadvantages of sclerotherapy mentioned earlier.

Endovascular vein surgery many times requires anesthesia as the patient is not always prepared or willing to support any type of possible discomfort or pain.

Three main anesthetic techniques are commonly used in varicose vein surgery: general anesthesia, central nerve block and tumescent anesthesia.

General anesthesia or central nerve block has many possible adverse effects such as muscle rigidity and airway irritation at induction, hypotension and bradycardia intraoperatively, nausea, vomiting postoperatively. Also, if used in day surgery, the time to discharge can be many hours after surgery.

Some skilled in the art use other techniques such as external application of cold, or topical anesthesia, but these are at times insufficient to provide adequate analgesia. Furthermore, there are other effects desired when carrying out anesthesia for vein treatment. Some tumescent liquids cause vein contraction and this allows for a more uniform and effective irradiation. Other liquids enhance laser radiation absorption properties of vein, again allowing for a more effective vein closure.

Both Tumescent Anesthesia and general anesthesia provide adequate relief from pain, but Tumescent Anesthesia minimizes blood loss, bruising and post procedural discomfort. It is a technique for delivery of large volumes of liquid in a perivascular area.

The word "tumescent" means swollen or firm. A large volume of liquid is delivered subcutaneously into target tissue. Dr. Jeffrey Klein, a dermatologist, first developed Tumescent Anesthesia, in liposuction techniques. He used a diluted solution of a local anesthetic, epinephrine, sodium bicarbonate and normal saline to numb the areas to be treated and to minimize the bruising and bleeding that would otherwise complicate any liposuction procedure. It improved patient safety, the precision of the liposculpture procedure and patient satisfaction and convenience.

In U.S. Patent Publication No. 2006/0253112, Suarez et al. propose, in cosmetic laser treatment device and method for localized lipodystrophies and flaccidity, a saline solution inserted into the treatment site to aid in the heating of fat cells and their eventual destruction as well as their removal. This was an advantage to prior art in that the tumescent solution applied also improved energy absorption of target tissue.

Goldman et al. proposed the use of tumescence in vein treatment with RF. In U.S. Pat. No. 7,396,355 they disclose a method and apparatus for applying energy to a hollow anatomical structure such as a vein, to shrink the structure. The invention is directed to pre-compressing and exsanguinating vein while providing anesthesia by delivering fluid to vein tissue in order to induce tumescence and consequent compression of the hollow anatomical structure during a procedure of applying energy from within the structure. The method described is specific of vein treatment techniques that apply RF energy and, as mentioned earlier, even in the case that the application of the disclosed method of tumescence, technique has proven to be ineffective in comparison to current state of the art. Furthermore, the procedure of exsanguination can be tedious and time consuming and in addition, it is not desired in endovenous laser treatments that apply laser wavelengths such as 980 nm which is highly absorbed by hemoglobin or 1470 nm which is highly absorbed by water, the main component in blood. Doing this would make procedure much less effective.

Tumescent anesthesia has been applied with increasing success in endovascular laser vein treatment. Once optical laser fiber is in place within the vein, before applying laser radiation, a considerable amount of tumescent solution is delivered subcutaneously. A common procedure is to make a number of percutaneous injections of a tumescent anesthetic agent under ultrasonic guidance along the entire length of the affected vein into the perivenous space. An appropriate method using tumescent solution should achieve local analgesia and constriction of the vein compressing the fiber inside it.

There are numerous disadvantages associated with this method of administering local anesthesia injections. It is tedious and time consuming because of the amount of necessary injections. Injections may be painful for the patient and leave puncture wounds. Finally, as pointed out by Holdstock et al. in some cases, the standard technique of tumescent anesthesia by needle injections may cause damage to laser fiber (J. M. Holdstock, P. Marsh, M. S. Whiteley, B. A. Price. *It is Possible to Cause Damage to a Laser Fibre during Delivery of Tumescent Anaesthesia for Endovenous Laser Ablation (EVLA), Eur J Vase Endovasc Surg* (2008) 36, 473-476).

In U.S. Pat. No. 7,163,533 Hobbs et al. propose a solution to address these problems. They claim a catheter device for treating vascular disease, comprising catheter to be inserted into blood vessel and including lumen(s) through which energy delivery device and fluid are received, and exits disposed in sidewall of catheter. The catheter device includes an energy delivery device such as an optical fiber for delivering laser energy and a catheter. The catheter lumen receives the optical fiber and a fluid such as an anesthetic agent or vasoconstricting agent. According to the invention, a plurality of exits is formed in the sidewall of the catheter. The exits are in communication with the catheter lumen and administer the fluid into the blood vessel, well before the leading treatment area and behind the fiber tip. This device and method are not ideal for effective laser treatment as tumescent liquid is released through the sides of catheter sheath and not up front, where laser fiber tip is and therefore not nearby the place where lasing will immediately take place. It teaches counter to the present invention.

Prior art mentioned above presents a series of possible complications when applying tumescent or other anesthesia in endovascular laser treatment of varicose veins, including temporary discomfort, swelling, bruising, areas of hyperpigmentation, and hematoma.

There is therefore a need for an improved method and device for providing anesthesia in vascular surgery. The improved method and device should eliminate possibility of pain, safely and without discomfort for the patient, while applying energy to a vein. It should also enable more efficient and enhanced treatment of the problem veins. Present invention addresses these needs.

OBJECTIVES AND BRIEF SUMMARY OF THE INVENTION

It is an objective of the present invention to provide a method and device for improved vascular treatment of venous insufficiency.

It is another objective of the present invention to provide a method and device for safer, painless and more reliable vascular treatment to accomplish an effective closure of insufficient veins.

It is yet another objective of the present invention to provide an endoluminar energy treatment method and device that minimize pain during and after the procedure and enhance treatment versatility.

It is still another objective of the present invention to treat insufficient veins avoiding the need of administration of large amounts of anesthesia around them.

It is also an objective of the present invention to provide a simpler method of treating insufficient veins that minimizes the possibility of harming patient or damaging fiber due to procedural errors by the physician.

Briefly stated, a method and device are disclosed for improved minimally invasive vascular treatments. The procedure comprises introducing a mono-channel or multichannel catheter into a vein to be treated, under local anesthesia, where the multichannels can be essentially concentric. This special catheter receives an energy transmitting elongate member in a channel and a fluid in another channel, or in the case of a mono-channel, fluid flows around the member Fluids that can be used, but not limited to, are saline solutions, cooled saline solutions, liquids for vapor generation, vasoconstricting agents, anesthetic agents and/or a formulation containing an ingredient which can be activated by the applied energy. Anesthesia, where used, is introduced inside of the vein, thus eliminating the need of external or tumescent anesthesia. In addition, the previously mentioned fluids can also be combined according to the treatment requirements for different purposes and effects. After catheter and energy-transmitting elongate member are correctly placed and locked, fluid is delivered at member's tip and energy is emitted while withdrawing the elongate member-catheter set, choosing appropriate energy parameters for each case. In a preferred embodiment an optical fiber is used as the elongate member and a laser as a light energy source. In a preferred embodiment 20 ml of 1% lidocaine are used. In another preferred embodiment, fluid is delivered by means of an infusion pump. In a preferred embodiment, the optical fiber is a radial emitting fiber and the wavelength used is 1470±30 nm. This new vascular treatment has advantages over prior art, including: less procedure time, an easier and more versatile technique and the possibility to check vein closure echographically during and after the energy treatment. The method and device can be used with a variety of energy sources including lasers, other light sources, RF power sources and thermo-electric means.

The above and other objects, features and advantages of the present invention will become apparent from the following description read in conjunction with the accompanying drawings (in which like reference numbers in different drawings designate the same elements).

DETAILED DESCRIPTION OF PREFERRED EMBODIMENTS

As previously mentioned, prior art vein treatments present numerous drawbacks. Sclerotherapy, for instance, may cause allergic reactions, skin burn and stains, and blood clots. In addition, treatment is limited to veins of a particular size and range as larger varicose veins may be more likely, according to many studies, to recur if treated with sclerotherapy. Vein stripping shows several disadvantages compared to other approaches: general, loco-regional or peridural anesthesia necessity (with their associated side effects); it may damage collateral branches of the vein with consequent bleeding, hematomas, or other complications such as blood loss, pain, infection, nerve injury and swelling. This invasive procedure involves damage to the treated area, leading to patient pain and discomfort for hours and even days after surgery. Finally, the use of RF energy in the treatment of vein insufficiency may be ineffective in certain cases and interventions can be lengthy and stressful for the patient. Nevertheless, it is still a popular local energy treatment among physicians. Laser procedures, represent minimally invasive treatment of blood vessels and overcome the majority of these disadvantages. They provide a closer access to the treatment area, allowing less powerful laser equipments and less damage to skin or to healthy tissue. This in turn reduces costs while at the same time provides a shorter recovery period due to less damage to skin and to surrounding healthy tissue. Laser procedures are safe, with low vein perforation risks, fast and easy to perform for those skilled in the art.

Regarding anesthesia, main drawbacks of commonly used techniques in prior art can be summarized. General anesthesia and central nerve block can cause muscle rigidity and airway irritation at induction, hypotension and bradycardia intraoperatively, and nausea and vomiting after surgery. If used in day surgery the time to discharge can be after several hours. In spite of tumescent anesthesia's improved hemostasis, reduced hematoma, hyperpigmentation, and pre-dissection of the vein from surrounding tissue, its success depends largely on surgeon expertise and precision of the injections. Also, when large volumes of solution are injected, the elimination of these fluids become an issue and may be at times inconvenient. Studies suggest that in some cases, this technique may cause damage to laser fiber.

Due to these drawbacks, delivery of liquids such as anesthesia, sclerosants, cold solutions, and/or formulations containing energy activated ingredients from the inside of the treated vein is proposed. Mainly, the procedure consists in providing an appropriate liquid solution directly inside the vein, where laser radiation is emitted, previously and/or during laser emission. This is accomplished by using special catheters, which allow passage of both an optical fiber and a fluid. Delivering fluid in the place where laser radiation occurs, improves treatment efficiency and safety over prior art, because fluid effects (anesthetic, vasoconstrictor, etc) are achieved before flushing away in the venous system.

As previously mentioned, the present invention describes methods and devices to perform anesthesia endoluminarily, i.e. from the inside of the vein (intravenous dripping anesthesia), thus eliminating the need of external or tumescent anesthesia. In addition, other substances can also be combined according to the treatment requirements for different purposes and effects. As a consequence, advantages beyond those of tumescent anesthesia can be accomplished, while avoiding main drawbacks of the classic tumescent technique.

The possibility of applying other substances besides anesthetics inside the vein, allows for improving and enhancing diverse treatment aspects according to different specific requirements. For example, radiation absorption can be enhanced by means of delivering a fluid that presents a high absorption coefficient within the range of the wavelength used, thus improving energy transference between optical fiber and venous tissue.

Intravenous dripping (endoluminar) anesthesia is ideally suited for lower extremity ambulatory surgery because it accomplishes good anesthetic effect while avoiding conventional tumescent anesthesia disadvantages. In contrast to other anesthetic techniques, such as general or spinal anesthesia, properly conducted intravenous dripping anesthesia avoids hemodynamic instability and pulmonary complications, facilitates post-operative pain management and timely discharge.

When intravenous anesthesia dripping techniques are used along with minimally invasive laser procedures, vein treatment can be accomplished with superb results, regarding efficient vein closure, safety, absence of pain, patient comfort and simplicity. Furthermore, the possibility of injecting other substances from the inside of the vein, improves treatment versatility, since different specific features can be enhanced.

The method and device disclosed in present invention, preferably uses vascular laser procedures, associated with intravenous (endoluminar) dripping anesthesia, taking advantage of their principal benefits, thus overcoming previously stated prior art's main drawbacks. They can also use other modalities such as radio frequency (RF), straight thermal, or chemical means for the procedures.

Figure 1:
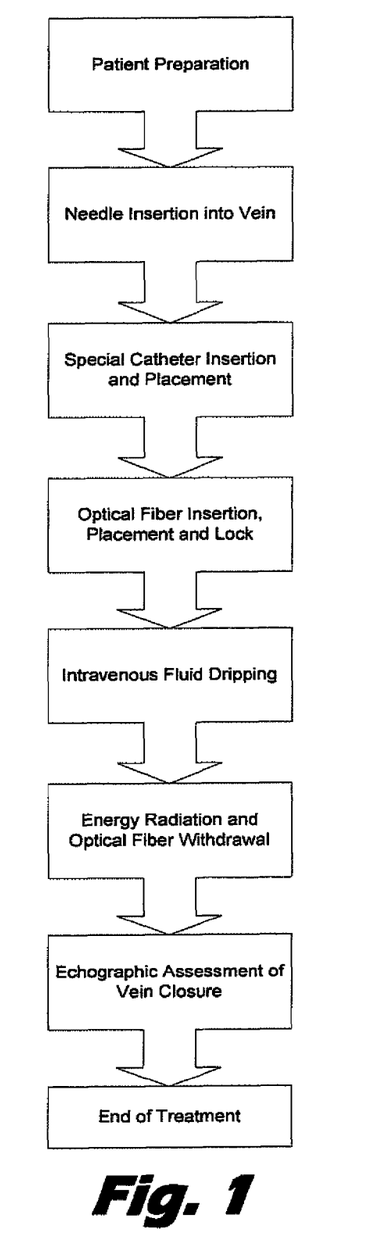
FIG. 1 depicts a preferred embodiment of present invention describing the main steps of a procedure disclosed.

In a preferred embodiment, depicted in FIG. 1, the procedure consists in performing an intravenous dripping anesthesia, in order to carry out an endoluminar treatment for insufficient veins. This is an excellent approach, in which advantages beyond those of tumescent anesthesia can be accomplished, while avoiding main drawbacks of the classic tumescent technique.

Basically, the procedure consists in inserting a needle through the skin into the vein to be treated and then an optical fiber, by means of a specially-designed catheter, under some local anesthesia. A typical procedure to carry out this task is to insert a guide wire inside the vein through needle's lumen. Once the guide wire is inserted, a dilator is used to slightly increase the size of the punction made onto the skin, in order to accomplish an easy catheter insertion. After catheter is inserted, guide wire is extracted and optical fiber is inserted through the catheter inside the vein and is advanced to the desired start position.

Some newly designed optical fibers (for instance, radial emitting fibers), due to their blunt tip and flexibility, allow carrying out the fiber insertion procedure without needing a guide wire. As a consequence, after inserting the needle, optical fiber is introduced directly through it (or a catheter) inside the vein, thus speeding up the whole vein treatment procedure.

Once catheter and optical fiber are correctly placed and locked, laser is activated. Afterwards, fluid is delivered at fiber's tip and laser radiation is emitted while withdrawing the optical fiber-catheter set, choosing appropriate irradiation parameters for each case. Fluid can be delivered before, during and/or immediately after laser radiation, according to the desired effect. As a consequence, closure of insufficient vein is achieved and the procedure ends.

In order to carry out anesthesia from the inside of the vein to be treated, different fluids can be delivered. Obviously, anesthetic agents may be used, usually diluted in saline solution or other appropriate liquid. In a preferred embodiment 20 ml of 1% lidocaine are used.

In a preferred embodiment, fluids are delivered by means of an infusion pump. As a consequence, improved control can be accomplished regarding volume and rate of administration (flow) of fluid.

Present invention describes embodiments in which optical fibers are inserted. However, it should be considered that any energy-transmitting elongate member can be used to perform the disclosed treatment, for example using RF energy or straight electrothermal means or chemical means.

Figure 2:
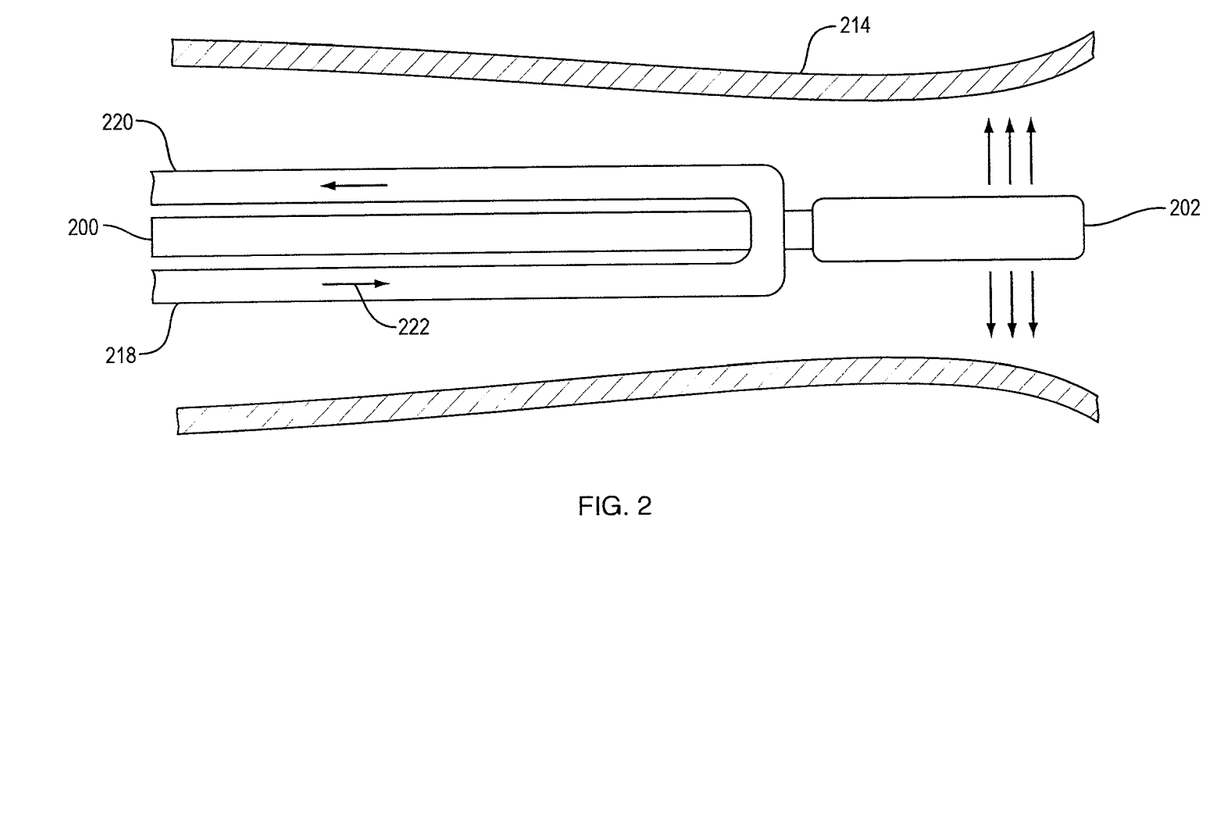
FIG. 2 shows a preferred embodiment of present invention where a catheter surrounding fiber is cooled by a liquid.

In another preferred embodiment, cooled saline solution can be used to achieve an anesthetic effect. FIG. 2 shows a preferred embodiment of present invention where a catheter surrounding fiber is cooled by liquid flowing back and forth internally through it. Catheter 200 surrounding fiber 202 is cooled by cold saline solution or water 222 flowing back and forth internally through it. This way, administration of tumescent anesthesia around the vein 214 is unnecessary and avoided. Cold temperature effect in the catheter 200 is achieved by permanently circulating liquid 222 through specific input 218 and output 220 channels. This circulation of cold liquid 222 reduces temperature in target structures by means of heat extraction, specifically due to heat conduction and convection. Alternatively, the vein can be flushed internally with cool water or saline solution, with a bit of anesthesia.

In another variant of this embodiment, device utilizes the cooling liquid or part of it for vapor generation at the energy emitting tip. According to this, as liquid reaches the energy emitting tip, energy is transferred to its molecules, thus fainting vapor. The advantage of using vapor comes from the fact that it can gently expand and reach all corners of the vein and the temperature of vapor is limited under atmospheric or close to atmospheric pressure to a fixed temperature such as 100° C., if water or saline solution is used. Thus, with a proper dose of liquid and energy, a well-defined quantity of energy is transferred to the vein wall and overheating can be moderated or prevented. In another embodiment, a separate liquid different from cooling liquid can be used for mentioned vapor generation.

In a preferred embodiment, optical fiber used is a radial emitting fiber and wavelength used is 1470±60 nm. Using radial emitting fibers allows for faster optical fiber insertion, minimizing perforation risks as well as pain during and after procedure due to even and uniform radiation. Since the 1470 nm wavelength is highly absorbed in water, which is the main component of tissues, low power densities can be used to efficiently, safely and reliably perform the vein treatment, also minimizing pain by treating only a minimum thickness of the vein walls to initiate closure.

As previously mentioned, present invention also comprises the possibility of applying other substances besides anesthetics inside the vein, thus improving and enhancing diverse treatment aspects according to different specific requirements. For example, radiation absorption can be enhanced by means of delivering a fluid that presents a high absorption coefficient within the range of the wavelength used, thus improving energy transference between optical fiber and venous tissue.

In a preferred embodiment, saline solution is administered to improve treatment efficiency. The procedure consists in delivering the saline solution near the fiber tip, and immediately lasing. This way, the zone to be irradiated accumulates water (due to the solution hypertonicity), and as the 1470 nm wavelength is highly absorbed in water, low power laser is enough to achieve efficient vein closure. Furthermore, hypertonic solution leads to vein spasm, thus enhancing the laser thermal effect.

In another preferred embodiment, a vasoconstricting agent is delivered endoluminarily to accomplish a reduction in vein diameter, in order to improve laser effect on venous tissue.

In addition to mentioned preferred embodiments, the method disclosed in the present invention can be performed by means of different optical fiber configurations, for example, bare fibers, side fibers, etc. and utilizing different wavelengths, for instance, 980 nm, 1320 nm, 1940 nm, etc.

In order to deliver fluid to the treatment site while applying an appropriate energy to the vein, different configurations are proposed.

Figure 3A:
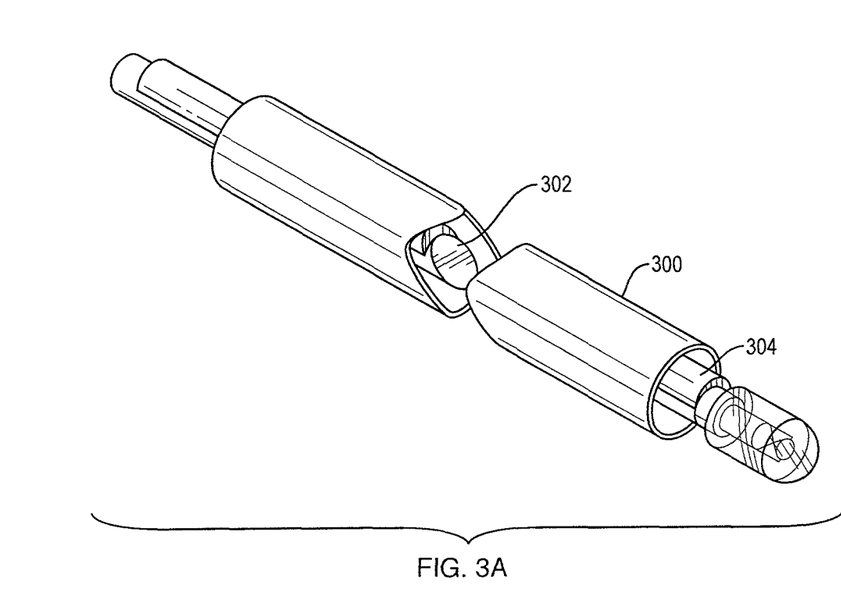
FIGS. 3a and 3b show a preferred embodiment, in which a tube and an optical fiber are inserted inside a catheter.
Figure 3B:
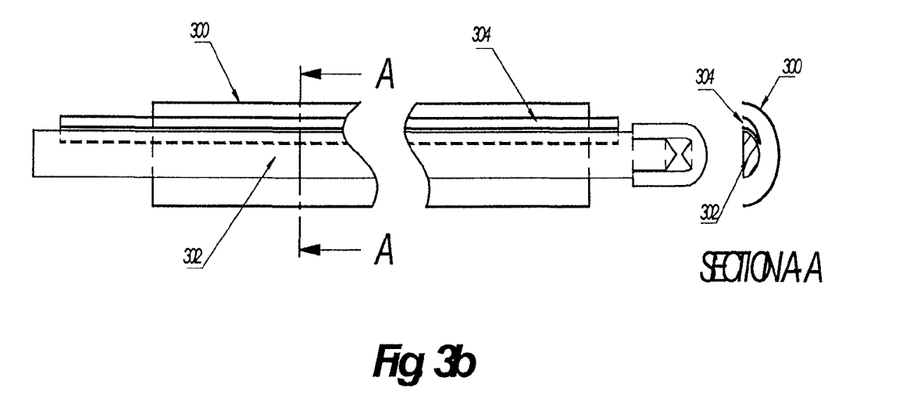

FIGS. 3a and 3b show a preferred embodiment, in which catheter 300 is positioned inside vein, and then optical fiber 302 is inserted in it, as previously explained. Special tube 304 is introduced inside catheter 300 and positioned parallel to the fiber. This tube is used to deliver a treatment fluid to the irradiation site. A low power laser source of 1470±60 nm is preferably used, set at below 10 W, or most preferably below 5 W.

Figure 4A:
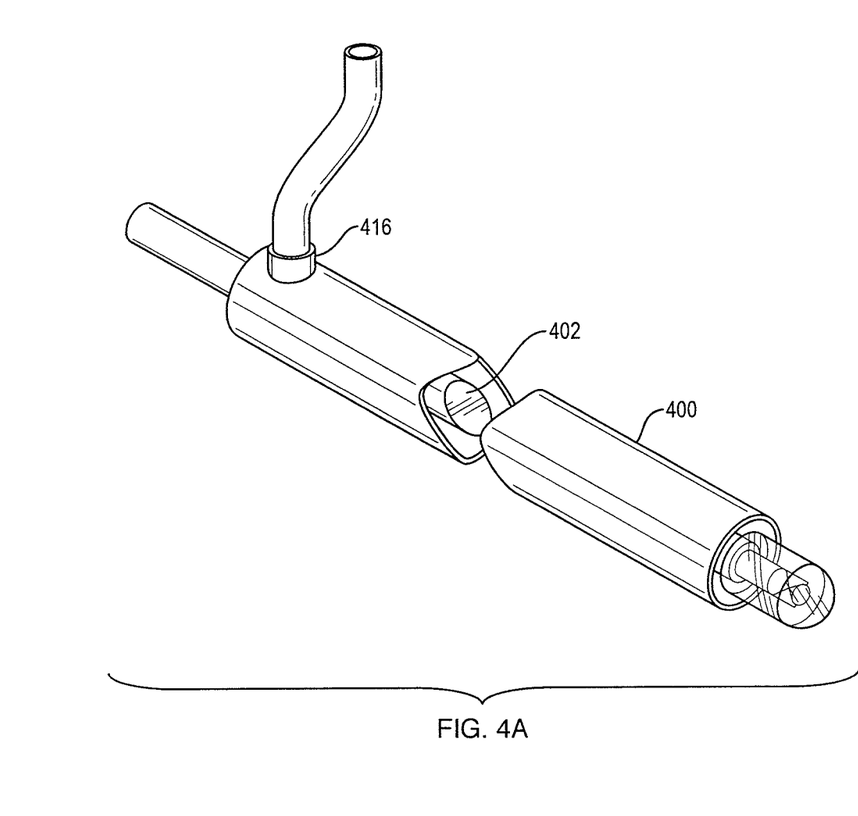
FIGS. 4a and 4b depict another preferred embodiment of the present invention, in which treatment fluid is delivered directly through catheter.
Figure 4B:
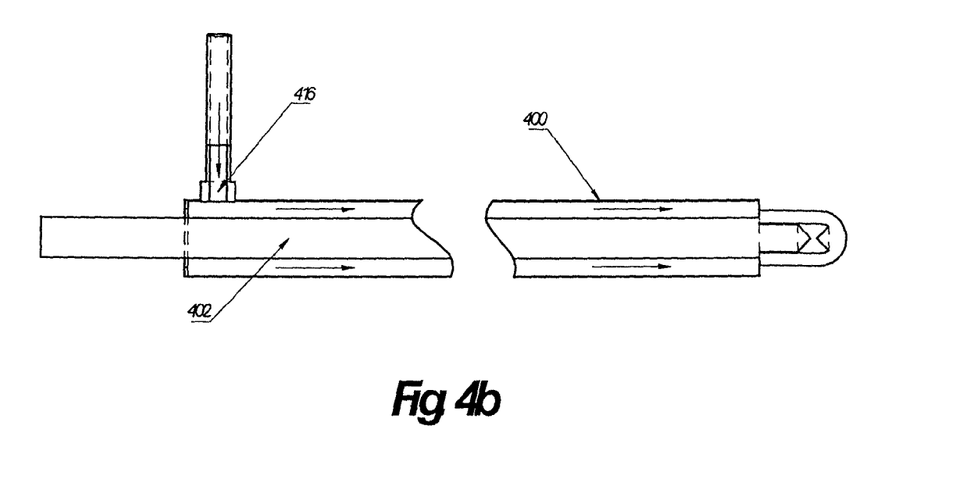

FIGS. 4a and 4b depict another preferred embodiment of the present invention, in which treatment fluid is delivered directly through catheter 400, without the need of using a special tube. This is done by injecting treatment fluid through stopcock 416 placed at the proximal end of the catheter 400.

Figure 5A:
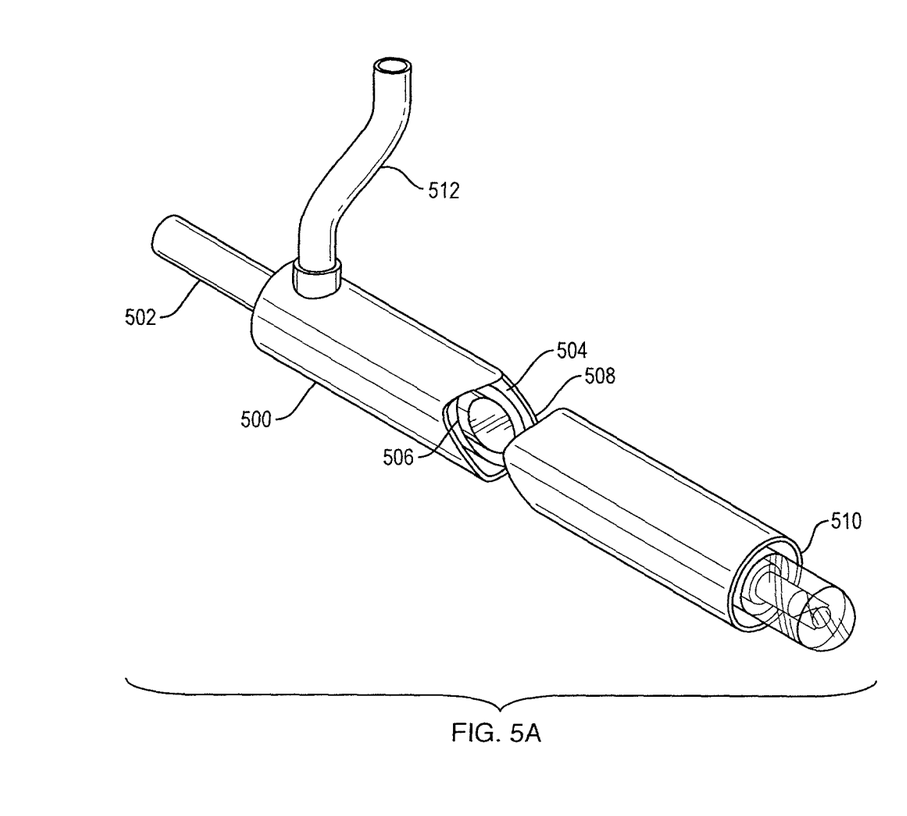
FIGS. 5a, 5b and 5c show another preferred embodiment of the present invention, in which catheter comprises a tube through which fluid is injected, and two concentric sleeves.
Figure 5B:
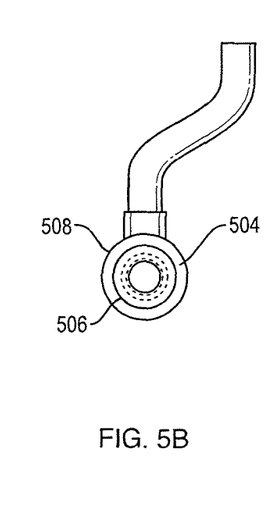

In another preferred embodiment, shown in FIGS. 5a and 5b, specially-designed catheter 500 is introduced inside the vein to be treated. Once in position, optical fiber 502 is inserted inside catheter 500 and advanced until its distal end protrudes beyond catheter 500, near the initial treatment area of the vein. Catheter 500 comprises tube 512, through which fluid is injected, and two concentric sleeves: interior sleeve 506 and exterior sleeve 508. Fluid is conducted through channel 504, formed by interior sleeve 506 and exterior sleeve 508, and is finally delivered at catheter's distal end 510, at the treatment site.

Figure 5C:
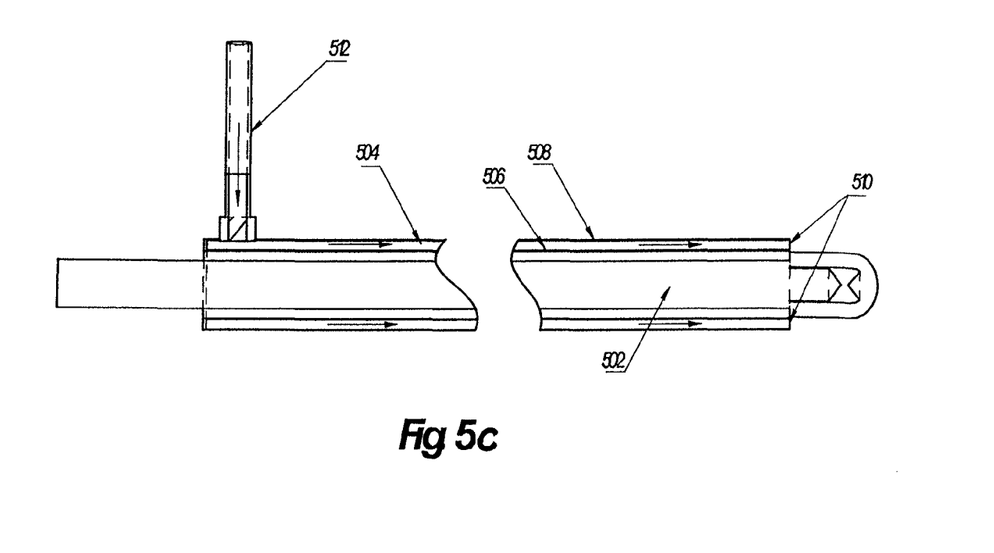

In another preferred embodiment, catheter's distal end 510 is closed and interior sleeve 506 can be slid relative to static exterior sleeve 508. Treatment fluid is confined between the two sleeves. Once the set is in the desired position inside the vein, physician gently pulls sliding interior sleeve 506 backwards a predefined distance, thus releasing treatment fluid at the zone to be treated. After delivering a desired amount of fluid (which depends on the delivery time period), interior sleeve 506 is slid back to its original position. Meanwhile and/or immediately after, laser radiation is administered to the vein. This way, precision of treatment fluid delivery is enhanced and can be controlled easily.

As mentioned previously, the catheter may have multiple channels through which different fluids and energy-transmitting elongate members can be used. Multichannel catheters enhance versatility and reduce treatment time.

The present invention is further illustrated by the following examples, but is not limited thereby.

EXAMPLE 1

According to the first disclosed embodiment, 15-20 ml of 1% lidocaine were used to perform intravenous dripping anesthesia. This local anesthetic is delivered endoluminarily into the vein, preferably after the active elongate member is introduced to the treatment site, as explained previously.

A radial emitting optical fiber is introduced through a special catheter inside the great saphenous vein, advanced to the desired start position and finally locked to the catheter. Once in position, the optical fiber is connected, at its proximal end to a 1470±60 nm diode laser source, which is activated and set at 6 W, in continuous mode. Meanwhile, the special catheter is connected to a fluid source containing the anesthetic solution previously mentioned. Then, the predetermined amount of anesthetic solution is delivered to the inside of the vein at the fiber's distal end and laser radiation is emitted from the optical fiber while withdrawing the coupled fiber/catheter. This procedure is repeated along the entire length of the treated vein, thus leading to vein's closure. In order to accomplish an efficient closure, 40-45 J/cm are applied to the treated vein, whose diameter can range from 10 to 12 mm. Lower energy densities of as little as 10-30 J/cm can also be used effectively with some veins.

As can be seen, no anesthesia other than intravenous dripping is used. In some cases, sedation can be added to diminish patient anxiety. According to experience, patients have little or no pain when treated with this endoluminar procedure.

EXAMPLE 2

According to another preferred embodiment of the present invention, saline solution may be administered to improve treatment efficiency. The procedure consists in delivering the saline solution near the fiber tip, and immediately lasing. This way, the zone to be irradiated accumulates water (due to the solution hypertonicity), and as the 1470±60 nm wavelength is highly absorbed in water, low power laser is enough to achieve efficient vein closure. Furthermore, the hypertonic solution leads to vein spasm, enhancing laser thermal effect. For example, 20% saline solution is delivered through a special catheter to the inside of the vein, before lasing. Volume of delivered solution is determined by physician according to vein characteristics as seen by echographic image, mainly the grade of insufficiency. Due to the previously described saline solution effect, only 3 to 5 W of laser power are sufficient to efficiently close a treated vein. Since the applied laser power and energy are relatively low and a substantial amount of cold fluid is injected inside the vein, no anesthesia is required to perform this treatment, because the thermal energy that is generated is low enough to avoid patient from feeling any pain.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method of treating veins, comprising:
   introducing a treatment device inside a vein;
   providing a cooling fluid directly inside the vein via a distal end of the treatment device to internally cool the vein;
   introducing an energy-transmitting member inside the vein via the distal end of the treatment device to irradiate the vein with energy;
   advancing a distal end of the energy-transmitting member to protrude beyond the distal end of the treatment device inside the vein; and
   irradiating said vein via the protruding distal end of the energy-transmitting member; and
   wherein a part of said cooling fluid is vaporized during the step of irradiating said vein.

2. The method according to claim 1, wherein the method is adapted to endoluminally treat vascular irregularities by internally cooling said vein before it is irradiated with energy from the energy-transmitting member within said vein.

3. The method of endoluminally treating vascular irregularities according to claim 2, wherein the step of providing the cooling fluid directly inside the vein comprises passing the cooling fluid through a channel in the treatment device, wherein at least a portion of said cooling fluid exiting near a distal end of said treatment device is vaporized.

4. The method for treating vascular diseases according to claim 1 wherein said internally cooling fluid includes a local anesthetic in it.

5. The method of endoluminally treating vascular irregularities according to claim 3, further comprising the steps of:
   introducing the treatment device inside the vein, to permit said cooling fluid to pass around said energy-transmitting member inside the vein;
   delivering energy and fluid to a treatment site via an exposed distal end of the treatment device; and
   treating said vascular irregularities with said energy.

6. An endoluminar method of treating vascular irregularities, comprising:
   providing a multichannel introducing device inside a vein;
   delivering a fluid via the multichannel introducing device to directly infuse a treatment site inside the vein with the fluid;
   introducing an energy-transmitting member to the treatment site inside the vein via a distal end of the multichannel introducing device;
   advancing a distal end of the energy-transmitting member to protrude beyond the distal end of the multichannel introducing device inside the vein; and
   irradiating the treatment site inside the vein via the protruding distal end of the energy-transmitting member;
   wherein the treatment site inside the vein is infused with the fluid prior to or simultaneously with energy emission from the protruding distal end of said energy-transmitting member.

7. The endoluminar method according to claim 6, wherein said multichannel introducing device is a catheter with at least two channels, wherein one channel is adapted for said energy-transmitting member to transmit energy, and another channel is adapted to deliver said fluid.

8. The method of endoluminally treating vascular irregularities according to claim 5, wherein said energy-emitting member is selected from the group consisting of an optical fiber, an RF transmitting device, and a thermal emitting device.

9. The method of endoluminally treating vascular irregularities according to claim 5, wherein said fluid is selected from the group consisting of a saline solution, a cooled saline solution, an anesthetic, and a formulation containing an ingredient that is activated by said energy emitted from said distal end of said energy-emitting member.

10. The endoluminar method of treating vascular irregularities according to claim 6, wherein said energy-emitting member is selected from the group consisting of an optical fiber, an RF transmitting device, and a thermal emitting device.

11. The endoluminar method of treating vascular irregularities according to claim 6, wherein said fluid is selected from the group consisting of a saline solution, a cooled saline solution, an anesthetic, and a formulation containing an ingredient that is activated by said energy emitted from said distal end of said energy-emitting member.

12. A device for treating veins, comprising:
   an energy-transmitting member adapted to emit energy to a vein from inside the vein; and
   a catheter configured to be positioned inside the vein;
   wherein the catheter is adapted to introduce a cooling fluid directly inside the vein and to introduce the energy-emitting member inside the vein;
   wherein a distal end of the energy-transmitting member is configured to protrude beyond a distal end of the catheter to irradiate the inside of the vein; and
   wherein a part of said cooling fluid is vaporized during irradiation of said vein.

13. The device according to claim 12, wherein the catheter comprises at least one channel for introducing said energy transmitting member and introducing said cooling fluid.

14. A treatment system for endoluminar treatment of vascular irregularities comprising:
   an energy-transmitting member adapted to emit energy to a vein from inside the vein; and
   a catheter configured to be positioned inside the vein;
   wherein a distal end of the catheter is adapted to introduce a cooling fluid directly inside the vein and to introduce the energy-transmitting member inside the vein, such that at least some of the cooling fluid is vaporized inside the vein by the energy emitted by the energy-transmitting member; and
   wherein a distal end of the energy-transmitting member is configured to protrude beyond the distal end of the catheter to irradiate the inside of the vein.

15. A treatment system for endoluminar treatment of vascular irregularities comprising:
   an energy-transmitting member adapted to emit energy to a vein from inside the vein; and
   a catheter configured to be positioned inside the vein;
   wherein the catheter comprises at least one channel for introducing the energy-transmitting member inside the vein and at least one channel for introducing a cooling fluid directly inside the vein and wherein a part of said cooling fluid is vaporized during irradiation of said vein; and
   means for timing said introduction of the cooling fluid and for timing energy emission from said energy-emitting member;
   wherein a distal end of the energy-transmitting member is configured to protrude beyond a distal end of the catheter to irradiate the inside of the vein.

16. The system according to claim 14, wherein said energy transmitting member is an optical fiber.

17. The system according to claim 16, wherein said optical fiber has a distal end, which emits radiation radially within said vein.

18. The system according to claims 14, wherein said introduction of the cooling fluid is accomplished with an infusion pump.

19. The system according to claims 14, wherein said cooling fluid is selected from the group consisting of a saline solution, a cooled saline solution, an anesthetic, a formulation containing an ingredient that can be activated by said energy emitted from said energy-transmitting member.

20. The system according to claim 15, wherein said energy transmitting member is an optical fiber.

21. The system according to claim 20, wherein said optical fiber has a distal end, which emits radiation radially within said vein.

22. The system according to claim 15, wherein said introduction of the cooling fluid is accomplished with an infusion pump.

23. The system according to claim 15, wherein said cooling fluid is selected from the group consisting of a saline solution, a cooled saline solution, an anesthetic, a formulation containing an ingredient that can be activated by said energy emitted from said energy-transmitting member.

24. The system according to claim 13, wherein said energy transmitting member is an optical fiber.

25. The system according to claim 24, wherein said optical fiber has a distal end, which emits radiation radially within said vein.

26. The system according to claim 12, wherein said introduction of the cooling fluid is accomplished with an infusion pump.

27. The system according to claim 12, wherein said cooling fluid is selected from the group consisting of a saline solution, a cooled saline solution, an anesthetic, a formulation containing an ingredient that can be activated by said energy emitted from said energy-transmitting member.

\* \* \* \* \*